(12) United States Patent
Bubien

(10) Patent No.: US 6,586,416 B2
(45) Date of Patent: Jul. 1, 2003

(54) METHODS OF TREATMENT USING AN EPITHELIAL SODIUM CHANNEL BLOCKER AND AN INHIBITOR OF THE MINERALOCORTICOID RECEPTOR

(76) Inventor: James K. Bubien, 2505 Elizabeth Dr., Pelham, AL (US) 35124

( * ) Notice: Subject to any disclaimer, the term of this patent is extended or adjusted under 35 U.S.C. 154(b) by 0 days.

(21) Appl. No.: 10/125,655

(22) Filed: Apr. 19, 2002

(65) Prior Publication Data

US 2002/0156057 A1 Oct. 24, 2002

Related U.S. Application Data

(63) Continuation-in-part of application No. 09/942,973, filed on Aug. 31, 2001
(60) Provisional application No. 60/284,515, filed on Apr. 19, 2001.

(51) Int. Cl.[7] .................... A61K 31/56; A61K 31/495
(52) U.S. Cl. ................................. 514/177; 514/255.06
(58) Field of Search ............................ 514/177, 255.06

(56) References Cited

U.S. PATENT DOCUMENTS 5,120,724 A * 6/1992 Fishman et al. ............ 514/177

OTHER PUBLICATIONS

Pratt, et al. "Blood Pressure Responses to Small Doses of Amiloride and Spironolactone in Normotensive Subjects", Hypertension, Nov., 2001.

* cited by examiner

*Primary Examiner*—Theodore J. Criares
*Assistant Examiner*—Jennifer Kim
(74) *Attorney, Agent, or Firm*—Glenna Hendricks; Lucy Hicks

(57) ABSTRACT

Co-administration of a channel blocking epithelial sodium channel (ENaC) blocker in conjunction with a mineralocorticoid receptor inhibitor makes it possible to achieve desired lowering of blood pressure with use in the range of 20% to 75% or less of the presently used dosage of the mineralocorticoid receptor inhibitor (MRI), thus avoiding many of the deleterious side effects usually associated with administration of an MRI. As little as 10% of the usual dosage of MRI may, in some cases, be efficacious. The most commonly used ENaC blocker now in use is amiloride. The most commonly used inhibitors of the mineralocorticoid receptor are precursors of canrenone.

2 Claims, No Drawings

METHODS OF TREATMENT USING AN EPITHELIAL SODIUM CHANNEL BLOCKER AND AN INHIBITOR OF THE MINERALOCORTICOID RECEPTOR

This application is a continuation-in-part of U.S. patent application Ser. No. 09/942,973, filed Aug. 31, 2001, now pending, which takes priority from Provisional Patent Application No. 60/284,515, filed Apr. 19, 2001.

This work was partially supported by a grant from the United States Government, Department of Health and Human Services, National Institutes of Health, DK-52789. Hence, the United States Government has certain rights in this invention.

FIELD OF THE INVENTION

This invention relates to the control of hypertension in patients suffering from aldosteronism and conditions wherein aldosterone may be elevated secondary to pathophysiological conditions as seen in patients with cardiac insufficiency such as in post-myocardial infarction. Simultaneous administration of an epithelial sodium channel (ENaC) blocker in combination with an agent that inhibits the mineralocorticoid receptor provides a new and effective means of treatment.

BACKGROUND ART

Aldosterone is involved in salt and water homeostasis. The main effect is thought to involve genomic mechanisms. These mechanisms are thought to be mediated by the mineralocorticoid receptor. However, the existence of plasma membrane steroid receptors has also been postulated.

The mineralocorticoid hormone aldosterone has the ability to cause an increase the reabsorption of salt and water. A part of this process appears to involve the stimulation of amiloride-sensitive sodium channels in the cortical collecting duct of the kidney. The classical mechanism of this regulation is that aldosterone activates a cytosolic mineralocorticoid receptor that, in turn, has genomic effects resulting in increased transcription of the genes that produce serum-glucocorticoid-regulated kinase SGK and $Na^+$—$K^+$ ATPase. A compelling reason for suspecting a genomic mechanism of regulation is that in vitro effects of aldosterone are not acute, but rather take as long as four hours to develop and can be blocked by inhibitors of transcription and translation. It is important to consider that the vast majority of experiments to elucidate the mechanism of action of aldosterone have been carried out on model systems such as rat tissue and cells and A6 epithelial cells derived from *Xenopus lavis*. The mechanism of action of aldosterone in other species, including humans, is more complex than in those model systems.

A body of evidence has been accumulating that suggests that in species other than the rat, aldosterone produces acute effects at picomolar concentrations. For example, rapid aldosterone-mediated effects on cellular processes in human smooth muscle cells and human lymphocytes have been observed when the mineralocorticoid receptor has been inhibited with spironolactone. Spironolactone is converted in the body to canrenone, the active metabolite, a compound of the formula:

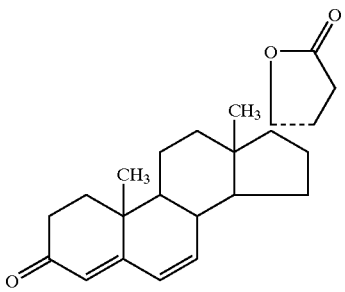

Formula I or to the canrenoic acid ion in the body. Canrenone, too, has been used as an aldosterone antagonist. (See U.S. Pat. No. 2,900,383, which is incorporated herein by reference in its entirety.).

Several articles compare use of spironolactone and amiloride in treatment of patients. For example, Jeunemaitre, et al. teaches use of, in the alternative, spironolactone, hydrochlorothiazide/amiloride combination or cyclothiazide/triamterene combinations in treatment of patients with elevated blood pressure. (See *American Journal of Cardiology*, 62 (16), pp 1072–7 (Nov. 15, 1988.) There is no suggestion therein to use spironolactone with amiloride.

Millar, et al report a study comparing amiloride and spironolactone (*British Journal of Clinical Pharmacology*, 18(3), pp. 369–75 (September, 1984)). (See, also, *Clinical Pharmacology & Therapeutics*, 27 (4), pp 533–43 (April, 1980).).

The administration of spironolactone in accord with present dosage standards, whether used alone or using previously taught combinations, is known to cause several serious and uncomfortable side effects, including dangerous alterations in blood potassium causing hyperkalemia. Endocrine disturbances, including enlargement of breasts in males, also occur.

BRIEF SUMMARY OF THE INVENTION

Co-administration of a channel blocking epithelial sodium channel (ENaC) blocker in conjunction with a mineralocorticoid receptor inhibitor makes it possible to achieve desired lowering of blood pressure with use in the range of 20% to 75% or less of the presently used dosage of the mineralocorticoid receptor inhibitor (MRI), thus avoiding many of the deleterious side effects usually associated with administration of an MRI. Usually the dosage of MRI is about 20% to 50% of that required when administered without an ENaC blocker, though as little as 10% of the usual dosage of MRI may, in some cases, be efficacious. When used at the lower levels, it is possible to avoid or decrease the more serious and/or distressing untoward reactions to the MRI.

DESCRIPTION OF THE INVENTION

It is the purpose of this invention to provide means for treatment/control of hypertension in patients suffering from aldosteronism, including conditions wherein elevated aldosterone levels may be secondary to other pathophysiological processes such as heart failure.

The rational for inhibiting the effects of aldosterone in patients with post-myocardial heart failure is that subsequent to damage to the heart muscle, the ability of the heart to function as an efficient pump is reduced. This reduction in pumping efficiency is the source of reduced cardiac output. When the body senses a reduction in cardiac output, the renin-angiotensin-aldosterone axis is activated as a compensatory mechanism. Activation of this mechanism causes the blood vessels to constrict and the blood volume to increase by retention of salt and water. This compensatory attempt by the body to adjust for the reduced cardiac output puts more strain on the damaged heart. Ultimately, the feed-back mechanism meant to protect the organism causes the damaged heart to be damaged further. Reducing the effects of salt and water retention resulting from the increased aldosterone breaks the feed-back cycle, thereby reducing the workload for the heart and preserving cardiac function. It has now been found that simultaneous administration of an epithelial sodium channel (ENaC) blocker in combination with an agent that inhibits the mineralocorticoid receptor (an aldosterone antagonist) as disclosed herein provides a new and effective means of treatment for patients suffering from untoward effects of both primary and secondary aldosteronism.

The most commonly used ENaC blocker is amiloride. However, related compounds may be used in practice of the invention. Some pteridines have been shown to have properties similar to amiloride. The most common substituted pteridine in use is triamterene. Similarly, other mineralocorticoid receptor inhibitors such as analogues of spironolactone, including as those identified in this disclosure, may be used in practice of the invention. It is possible, when using the combination therapy, to reduce the amount of the MRI by 25% to 90%. For example, spironolactone is usually given at dosage of 25 to 100 mg. When used with a ENaC blocker such as amiloride, the dosage of as little as 5 mg. may be used. An aspect of the invention comprises compositions containing an ENaC blocker in combination with much smaller doses of an MRI than was previously delivered to have clinical significance.

Materials and Methods:
Principal Cell Preparation

Collecting ducts were manually dissected from sagittal slices obtained from 50 gram Sprague Dawley rats and 0.5 Kg New Zealand White rabbits. The dissected collecting ducts were suspended in RPMI 1640 culture medium supplemented with 1.5 mg/ml collagenase A (Boehringer Mannheim, Mannhein, Germany). The collecting ducts were enzymatically digested for 1.5 hours to isolate individual cells. The digested cells were washed in serum-free RPMI and placed in a perfusion chamber mounted on the stage of an inverted microscope. The whole-cell patch clamp configuration was established and initial current measurements were made in un-supplemented RPMI. The bath solution was changed (by perfusion of the entire bath chamber) to RPMI supplemented with aldosterone (100 nM), vasopressin (250 nM), amiloride (2 $\mu$M), spironolactone (1 $\mu$M), or various combinations of these compounds. To block the cytosolic mineralocorticoid receptor, some cells were suspended in RPMI supplemented with spironolactone for 1 hour prior to whole-cell patch clamping.

Preparation of Lymphocytes

Human and canine lymphocytes were isolated from peripheral blood samples by differential centrifugation over ficoll paque (Pharmacia Biotech, Uppsala, Sweden). The cells were washed and re-suspended in serum-free RPMI. Subsequently, suspended cells were placed in the perfusion chamber. Whole-cell patch clamp and testing of aldosterone were carried out using identical techniques and protocols as described for principal cells. Rabbit, rat and mouse lymphocytes were obtained by mincing sections of spleen and manually freeing the cells by agitation. The cell suspensions were then centrifuged over ficoll paque and treated identically to the lymphocytes obtained from peripheral blood. All procedures were carried out under the guidelines for animal use and with institutional board approval for human use.

Studies were conducted using both whole cell patch clamp and single channel patch clamp techniques. Whole-cell clamped rabbit principal cells were exposed to 100 nM aldosterone. Positive identification of these cells was determined by the response to either aldosterone, or, if the cells failed to respond to aldosterone, a positive response to vasopressin. No cells failed both tests. Upon entering the bath, the aldosterone induced a specific activation of the inward currents at hyperpolarized membrane potential clamp voltages. The activated currents were subsequently inhibited completely with 2 $\mu$M amiloride (in the continued presence of aldosterone), confirming that the activated currents were amiloride-sensitive. The average current-voltage relations for the current activated by aldosterone and the current inhibited by amiloride after aldosterone activation was studied. The current voltage relations showed inward current up to (+40 mV). $E_{Na+}$ was approximately +60 mV with the ionic gradients present. The activated current was carried exclusively by sodium. In a separate set of experiments rabbit principal cells were re-suspended in RPMI supplemented with 1 $\mu$M spironolactone for 1 hour prior to use for whole-cell patch clamp. This concentration is sufficient to inhibit completely the mineralocorticoid receptor. It was found that spironolactone had no effect on the inward currents. However, even with mineralocorticoid receptor inhibition, 100 nM aldosterone specifically activated the inward currents. These studies indicate that the acute activation of ENaC by aldosterone did not utilize the mineralocorticoid receptor and was, therefore, non-genomic.

In contrast to the findings in the rabbit principal cells, aldosterone had no acute affect on principal cells isolated from the collecting ducts of rats. Since aldosterone had no effect, the expression of ENaC and the cell type (principal cell) was confirmed in every study by subsequent acute specific activation of the amiloride sensitive inward currents by 250 nM vasopressin. The same protocol was carried out on rabbit principal cells. Once ENaC was activated by aldosterone, subsequent stimulation with vasopressin did not activate the inward currents any further, i.e., there was no synergistic effect of the two ENaC agonists, implying that they activated the same set of channels.

Studies were done to evaluate the average current activated by these ENaC agonists measured at $E_{K+}$. At this potential (−80 mV) there can be no potassium current. Thus, all of the current activated by aldosterone or vasopressin must be sodium current. In the absence of aldosterone, or if aldosterone activation was inhibited, vasopressin activated the inward currents. Statistical analysis of the mean current showed that for rat principal cells, aldosterone did not alter the current, but vasopressin increased it significantly, while amiloride restored the current to the basal level. For the rabbit principal cells, aldosterone significantly increased the current, vasopressin had no additional effect, and amiloride returned the conductance to the basal level. Also, the basal conductance and the activated conductance in rat and rabbit principal cells were not significantly different between the species.

The hypothesis that aldosterone-mediated non-genomic activation of ENaC utilized methylation rather than protein Kinase A-mediated phosphorylation to induce channel activation was tested. It was found that methyl esterification was independent of vasopressin-stimulated cAMP-mediated signal transduction.

Further studies that were conducted that directly demonstrated the findings on intact rabbit cortical collecting ducts helped to resolve an apparent contradiction. A considerable delay (2–4 hours) was observed when the in vitro effect of aldosterone was measured using intact renal collecting duct segments. In the present study aldosterone-stimulated ENaC activation was observed within seconds. The only obvious difference between former studies and the present study was that it was possible to control the cytosolic (ATP), whereas in intact collecting duct segments the cellular ATP is controlled by cellular metabolism. Full ENaC activation was only observed in rabbit principal cells when the pipette solutions were supplemented with a minimum of 2 mM ATP.

The "ragged" morphology of the whole-cell currents in principal cells and lymphocytes has generated some concern about the identity of the channels that are activated by aldosterone. To address this concern, single channel characteristics of the sodium conductors expressed by human lymphocytes were studied. It was found that conductance was the same as the channel conductance reported for human ENaC expressed in *Xenopus oocytes*.

To test the amiloride sensitivity of the single channels, outside-out patches were formed because amiloride only interacts with the outside surface of the channels. A "run-down" phenomena typical of ENaC in the inside-out patch experiments was noted. Incomplete inhibitory action of amiloride on these channels at an amiloride concentration close to $IC_{50}$ for amiloride and ENaC (75 nM) was found. When the amiloride concentration was increased to 2 $\mu$M, single channel activity was completely abolished.

When the cells were treated with 100 nM aldosterone, a somewhat different channel behavior was observed. In outside-out patches, the unitary conductance was unchanged, but the channels opened and closed in groups. Single channel activity was virtually abolished when amiloride (2 $\mu$M, final concentration) was added to the bath solution. Hence, it was demonstrated that this single channel behavior produced the "ragged" whole-cell currents that are characteristic of the sodium conductance of principal cells and lymphocytes by reconstructing the whole-cell currents from single channel recordings.

Finally, it should be mentioned that the vast majority of patches (>80%) were devoid of single channel activity in cells that were not pretreated with aldosterone. These single channel findings are completely consistent with the whole-cell findings, and establish, by biophysical characteristics, that the channels that are activated by aldosterone are ENaC.

The direct electrophysiological findings from these studies address three major issues concerning the role of aldosterone in the regulation of Na$^+$ currents by principal cells. First, the findings demonstrate directly an acute, non-genomic activation of an amiloride-sensitive sodium conductance (ENaC) in renal principal cells of the rabbit. In contrast, the findings also show that aldosterone fails to activate any current in principal cells of rats. Because the kidneys of both species are used extensively to study renal salt and water regulation, this difference has wide-ranging implications for understanding of the role of aldosterone in controlling sodium reabsorption in the collecting duct. For example, based on numerous previous studies indicating that aldosterone increases expression of epithelial sodium channels by interaction with the cytosolic mineralocorticoid receptor, inhibition of this receptor by spironolactone has been the recognized treatment for primary aldosteronism. However, these new studies show that aldosterone has the ability to activate nascent channels in the presence of spironolactone. Thus, a more effective therapy involves administration of an epithelial sodium channel (ENaC) blocker in combination with an agent that inhibits the mineralocorticoid receptor. One such combination is spironolactone and amiloride as a preferred treatment for patients suffering from aldosteronism where surgery is not warranted or cannot be performed, and in patients suffering from heart failure such as that seen in post-myocardial infarction.

Some previous studies utilizing rabbit cortical collecting ducts showed delayed effects of aldosterone on sodium conductance but failed to show the immediate effect that was demonstrated in the whole-cell studies of the effects as described. Hence, the therapy taught herein was not suggested by the previous findings. Since some of the studies measured trans-epithelial potential (TEP) and could demonstrate an acute change in TEP induced by vasopressin but not by aldosterone, the prior findings suggested that aldosterone did not produce an acute ENaC activation in rabbit CCD, contrary to the whole-cell clamp findings presented herein. The re-supplying cytosolic ATP, by using ATP-supplemented pipette solutions, made it possible to replete ATP to a sufficient concentration. This is not possible in intact collecting ducts in vitro. These findings show that the appropriate level of ATP was essential for signal transduction between aldosterone and ENaC to produce non-genomic ENaC activation. This demonstrates directly that aldosterone-stimulated signal transduction for ENaC regulation requires ATP from a depletable pool, but vasopressin-stimulated signal transduction for ENaC activation may utilize ATP from a pool that is not depleted. This line of reasoning reconciles the difference between the whole-cell clamp findings and the findings obtained in intact collecting ducts, because in intact tubules the in vitro metabolism may not be robust enough to continuously provide the cellular concentrations of ATP that are required for aldosterone-mediated ENaC regulation.

While spironolactone is exemplified as the more commonly used MRI, canrenone or other agents of the formula:

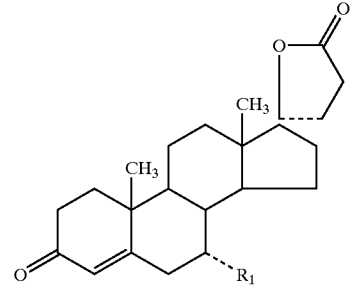

Formula II wherein $R_1$ is a protective group such as a carbonyl or carboxyl, or a sulfur-containing analogue of such groups which, when removed during metabolism, converts to the canrenone of Formula I, would be appropriate for use in compositions and in the method of this invention. For example, in the case of spironolactone, $R_1$ is $SCOCH_3$. However, other compositions containing as an active agent the analogue wherein $R_1$ is $COCH_3$ are also known and can be used in accord with the teachings herein. For example, $R_1$ may be a thio group, a carbonyl or a carboxyl group having 1–10 carbon atoms. $R_1$ may, for example, be $SCO—R_2$, $COR_2$ or $COOR_2$ wherein $R_2$ is alkyl, phenyl, phenylalkyl or alkenyl having 1–10 carbons, wherein the alkyl and alkenyl groups may be branched and phenyl may have an alkyl substituent. Any $R_2$ may, additionally, be substituted with 1-2 halo, amino or alkoxy moieties. Any metabolic precursor of canrenone would clearly be useful for purposes of the invention.

For purposes of treating hypertension in patients suffering from aldosteronism, various active agents which are epithelial sodium channel (ENaC) blockers can be given in combination with agents that inhibit the mineralocorticoid receptor. The range of dosage for co-administration may be within the parameters of dosage presently used when the active agents are administered separately for purposes of inhibiting mineralocorticoid receptor activity or as ENaC blockers.

It would be preferable to combine the active agents in one dosage form, if possible. For example, in a preferred embodiment of the invention, compositions containing 5 mg to 20 mg. spironolactone and 1 mg to 5 mg of amiloride would be administered twice daily to the average adult person. However, the combination therapy makes it possible to use far less of the spironolactone, as little of 5 mg. in adults and 1 mg. for children. The form of the composition would be determined by the condition of the patient and the particular agents administered. Preferred dosage would be 2–15 mg. spironolactone and 0.5 to 5 mg. amiloride.

EXAMPLE

Combine:
15 mg spironolactone
5 mg amiloride HCl
10 mg. lactose
100 mg. starch

The mixture is pressed into a tablet for oral administration.

EXAMPLE

Combine:
10 mg. spironolactone
2 mg. amiloride HCl
10 mg. lactose
5 mg. polyethylene glycol
100 mg. starch The mixture is pressed into a tablet for oral administration.

EXAMPLE

A mixture containing 10 mg spironolactone, 5 mg. amiloride HCl and 250 mg. starch is prepared and enclosed in a capsule for oral administration.

EXAMPLE

A mixture containing 10 mg. canrenone, 25 mg. of triamterene, 15 mg. polyethylene glycol, 50 mg. methylcellulose and 100 mg. starch is prepared and inserted into in a capsule for oral administration.

EXAMPLE

A mixture containing 5 mg. spironolactone, 2 mg. amiloride, 15 mg. polyethylene glycol and 20 mg. of methylcellulose and 100 mg. starch is prepared and inserted into a capsule for oral administration.

The compositions prepared in accord with standard methods are usually administered twice daily. Compositions in the form of suspensions or inclusion complexes such as cyclodextrin inclusion complexes, may also be used, though tablets and capsules would be the more commonly used dosage forms.

It would also be advantageous to provide the two active agents in separate compositions but packaged together in single dosage packets for purposes of assuring that the two agents are administered in combination and in appropriate combined dosage for purposes of ensuring that the benefits from administration of an ENaC blocker and mineralocorticoid receptor inhibitor are delivered to the patient in a safe manner. For example, the two medications providing appropriate combination of dosages could be packaged together in packets containing both agents for use in the methods of the invention to control dosing of the patient when the combination therapy is used.

What we claim is:

1. A method of controlling hypertension in patients suffering from aldosteronism comprising essentially simultaneous administration of 0.5 to 5 mg amiloride and 2–15 mg spironolactone.

2. A composition of matter comprising, in combination, 2–15 mg spironolactone and 0.5 to 5 mg amiloride in a carrier.

* * * * *